United States Patent [19]
Gilpatrick

[11] Patent Number: 4,813,062
[45] Date of Patent: Mar. 14, 1989

[54] RADIO-OPAQUE MARKER AND METHOD

[75] Inventor: Michael W. Gilpatrick, Chesnee, S.C.

[73] Assignee: Milliken Research Corporation, Spartanburg, S.C.

[21] Appl. No.: 896,181

[22] Filed: Aug. 13, 1986

[51] Int. Cl.$^4$ .............................................. H05G 1/28
[52] U.S. Cl. .................................. 378/162; 378/210; 378/62; 250/302
[58] Field of Search ............................ 378/162–165, 378/210; 250/302, 358.1

[56] References Cited

U.S. PATENT DOCUMENTS

| | | | |
|---|---|---|---|
| 2,439,374 | 4/1948 | Leader et al. | 378/165 |
| 2,462,018 | 2/1949 | Wood | 378/165 |
| 3,508,551 | 4/1970 | Walters et al. | 128/296 |
| 3,839,637 | 10/1974 | Willis | 250/302 |
| 4,506,676 | 3/1985 | Duska | 378/162 |

FOREIGN PATENT DOCUMENTS 2459866 6/1976 Fed. Rep. of Germany ...... 378/165

*Primary Examiner*—Craig E. Church
*Assistant Examiner*—John C. Freeman
*Attorney, Agent, or Firm*—George M. Fisher; H. William Petry

[57] ABSTRACT

A crayon-like marker is described which is capable of making marks detectable by X-ray on various substrates, e.g., textile products. The marker is comprised of a waxy medium in which is dispersed a radio-opaque substance. Additional coloring agents may be added if desired.

6 Claims, 1 Drawing Sheet

U.S. Patent   Mar. 14, 1989   4,813,062
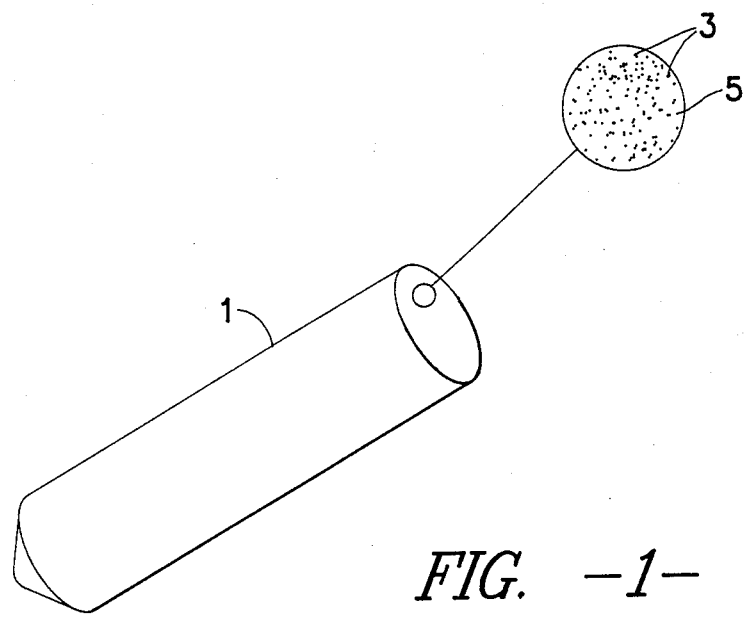
FIG. -1-
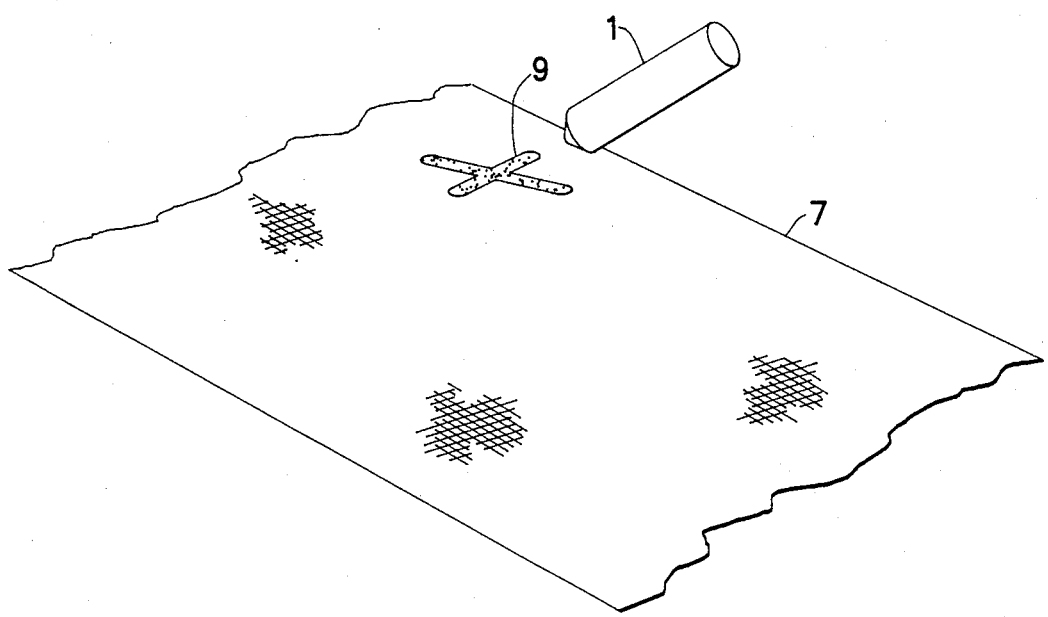
FIG. -2-

RADIO-OPAQUE MARKER AND METHOD

This invention relates to a method of making objects which may be later inspected using X-ray techniques. In particular, this invention relates to a marker which may be used to mark, in an unobtrusive manner, textile substrates, yarns, or other objects for purposes of locating defects or identifying components which would otherwise be difficult or impossible to detect visually. The marks made by such marker may be readily detected using conventional X-ray apparatus.

X-ray techniques are frequently used in applications where components which are ordinarily hidden from view must be observed or inspected. For example, airframe and aircraft engine manufacturers may use X-ray techniques to detect structural flaws and confirm proper assembly of air frames and aircraft engines. Generally, such inspections require some means to identify or make visible principal elements within the X-ray field of view, for example, the outline of a particular component or set of components within the object to be inspected, or require some means to draw attention on the X-ray image to a particular region of interest. It is also frequently desirable to provide some means to allow identification of the particular manufacturing batch or lot number or origin of manufacture of one or more components hidden from direct view.

Presently, these objectives frequently have been met by use of a radio-opaque metal marker or pointer made from, or perhaps painted with, a radio-opaque material, or by use of adhesive-backed tape carrying a radio-opaque substance, which has been placed on the part or parts of interest. For example, small sections of adhesive-backed foil made primarily of lead are commonly used for these purposes. Use of such foils or other adhesive backed markers are not satisfactory for many applications, especially where the adhesive used is not effective in maintaining the position of the marker, or in cases where it is either difficult or impossible to place a foil or tape on or in the desired object, or to remove the marker after X-ray inspection has been completed. Furthermore, such foils or tapes are expensive to manufacture, and can comprise a potential health hazard, particularly if lead is involved.

It is contemplated that liquid inks or paints, to which radio-opaque material has been added, may be used for the purpose of marking or identifying objects under X-ray illumination. However, such liquids may not be suitable for use with porous or semi-porous items (such as textile products) because of the tendency of the liquid to migrate, via capillary action or forces induced by the manufacturing process, into areas not intended to be marked, and because of the need to allow such liquids to dry before they contact other objects not intended to be marked. Also, such liquids can create a potential health hazard if inhaled, in the form of aerosols or vapors, during the application process.

The invention described herein provides a relatively safe, effective, and convenient means to mark a wide variety of objects for which the conventional techniques discussed above would be unsatisfactory. The following description refers to the accompanying figures, in which FIG. 1 depicts a crayon embodying the invention disclosed herein, and FIG. 2 depicts a crayon used to mark a substrate containing textile yarns in accordance with the invention disclosed herein.

In a preferred embodiment, a crayon or marking pencil 1 such as is depicted in FIG. 1 comprised of a solid radio-opaque substance 3 such as finely powered bismuth trioxide ($Bi_2O_3$), uniformly dispersed within a waxy medium 5 such as paraffin wax, is used as a marker to apply a mark to the object to be inspected or marked. It is believed other heavy metal containing compounds (such as an oxide, sulfide, sulfate, nitrate, etc.) of bismuth, lead, cadmium, barium, or other suitable element having an atomic number greater than about 56 may also be used, or may be preferred in certain circumstances. The relative proportion of the dispersed radio-opaque substance to the dispersing medium, the relative granularity of the radio-opaque substance, the absolute amount of the radio-opaque substance deposited, as well as other factors, will determine the visual contrast observed on the X-ray image, while the extent to which the dispersing medium rubs off and/or adheres to the object being marked, as well as the color of any pigment or other coloring agent additionally introduced into such medium, will determine the visual contrast generated by the crayon. Certain radio-opaque substances contemplated herein, due to their inherent color in the medium, may make the addition of additional pigments or coloring agents unnecessary. Therefore, depending upon the application, the crayon can make a mark which, while being quite prominent when seen in an X-ray image, could be either prominent or unobtrusive to the unaided eye when viewed under ordinary illumination, depending upon the nature of the radio-opaque substance and whether an additional coloring agent is used. It is contemplated that, optionally, the crayon could contain, in addition to the radio-opaque substance, a suitable conventional fluorescing composition which would provide enhanced contrast when viewed under appropriate illumination, for example, ultraviolet illumination.

It is contemplated that, while paraffin wax is a preferred dispersing medium, any suitable wax-like, resin-like or rosin-like material having a melting point over about 110° F., and into which a suitable radio-opaque substance may be dispersed, may be used. For example, appropriate hydrocarbon waxes, polyethylene oxides, or low molecular weight polyethylenes may be used. In some applications it may be difficult or inconvenient to apply a mark which is sufficiently observable, either because the mark is not sufficiently durable, or because of difficulty in applying a sufficient quantity of marker material. For example, certain applications may require that beeswax or various glues be employed as the dispersing medium; these substances may be relatively hard, i.e., exhibit high cohesion. If, for example, a relatively soft textile fabric is to be marked with a material which can withstand the various dyeing and finishing operations to which the fabric may be later subjected, it may be necessary to use a dispersing medium which is relatively hard, and which therefore may be rather difficult to transfer to the fabric without high applicator pressure. In such cases, it is contemplated that a crayon comprised of such dispersing medium may be applied by using an appropriate solvent, or by using a heat source such as a heat gun or a device similar to a conventional hot melt glue gun.

In one embodiment of this invention such as depicted in FIG. 2, a crayon containing a radio-opaque substance may be used by a textile inspector to mark areas of a moving textile substrate 7 or substrate component (for example, textured yarn) which contains an objectionable defect with a small quantity of abraded crayon material 9. Depending upon the ultimate end-use of the fabric, the defect detection protocol, the number of allowed defects, as well as other factors, the crayon may be pigment impregnated or tinted to a color which tends to maximize or minimize the visual contrast of the marks.

It is customary in the textile industry to transport and store textile fabrics during various stages of the manufacturing process either in the form of large wound rolls of a continuous web of fabric, or in the form of stacks of discrete sections of cut fabric. Manufactured yarn is also stored in wound rolls prior to its fabrication into textile fabrics. In either case, marks made during various inspection stages on all but the outermost portion of the fabric rolls or stacks or yarn rolls are hidden from view by the outer layers of fabric or yarn. Use of a radio-opaque marking material to mark desired portions of the fabric or yarn prior to winding on a roll, in conjunction with an appropriate conventional X-ray device, allows observation of the number, size and position of marks within the roll, which marks would otherwise be undetectable.

It is further contemplated that this technique may also be used to tag or identify yarn, scrims, or other textile products which are integrated into other products. For example, marks identifying the manufacturer may be placed on the yarn, scrim material, etc. to be integrated into an industrial belt or vehicle tire. Through the use of conventional X-ray apparatus, such marking will allow identification of the manufacturer of the yarn or scrim at any time during the life of the assembled belt or tire.

EXAMPLE 1

A radio-opaque crayon was made by melting paraffin wax, and adding to the melt approximately 35 percent (by weight) of lead (mono) oxide, PbO, in fine powder form. The mixture was stirred continuously while the temperature was lowered, so as to keep the dense lead compound uniformly suspended in the paraffin dispersing medium. At a temperature of approximately 110°-120° F., the mixture was soft and pliable, and was shaped into a generally cylindrical crayon shape, and then allowed to cool completely to room temperature. This same procedure was also used to make crayons containing the same medium, i.e., paraffin, but using powdered barium sulfate ($BaSO_4$) in one case and using powdered bismuth (tri)oxide ($Bi_2O_3$) in the other, using the same relative proportions. Thus, a total of three different crayon species were made.

Small swatches of a woven textile fabric were marked using all three crayons made as described above. The swatches so marked were then examined using a conventional X-ray inspection machine having a video display, using X-ray tube voltages ranging from 30 kilovolts to 90 kilovolts and using X-ray tube plate currents ranging from 2 milliamperes to 30 milliamperes. The resulting X-ray images showed the marks easily; the presence of the radio-opaque substances allowed a lower intensity of X-rays to penetrate, as compared to the surrounding areas.

Swatches marked as described above were also placed between unmarked fabric, thus hiding the marks from direct view. In this simulation, the marks were not visible. Again, X-ray inspection techniques as described above allowed an easy observation of the marks hidden within the structure, due to the presence of the radio-opaque substances.

EXAMPLE 2

A radio-opaque crayon was made by melting paraffin wax, and adding to the melt approximately 50% (by weight) finely divided bismuth (tri)oxide ($Bi_2O_3$). The mixture was stirred continuously while the temperature was lowered, in order to assure relatively uniform dispersion of the radio-opaque bismuth compound. At a temperature of approximately 110°-120° F., the mixture was soft and pliable, and was shaped as in Example 1. The marking of small swatches was performed as in Example 1, with similar results, except that enhanced contrast in the X-ray image was noted. Because of the yellow color of bismuth trioxide in the melt, visual contrast of marks made with this crayon on yellow swatches was minimal, and the marks made on such substrate were quite unobtrusive.

EXAMPLE 3

The procedures of Example 2 were followed, except that a small quantity (about 1.5% by weight) of carbon black was added to the melt. The result was a radio-opaque crayon capable of generating marks on light-colored (e.g., yellow or white) fabric swatches which showed significantly increased visual contrast compared with the crayon of Example 2.

Although the preferred embodiment of the invention has been described, it is contemplated that changes may be made without departing from the scope or spirit of the invention and it is desired that the invention be limited only by the scope of the claims. For example, the relative proportion of radio-opaque material to dispersing medium may be varied over a wide range, limited primarily by the degree of X-ray contrast desired (higher proportions yielding higher contrast) and the mechanical properties of the crayon (proportions higher than a certain material-dependent threshold yielding poorer mechanical stability).

I claim:

1. A marker for placing marks on a surface of an object, which marks are detectable under X-ray illumination, said marker comprising a dispersing medium in which is dispersed a single radio-opaque substance, said dispersing medium being solid at room temperature but, when brought into operable contact with the surface of an object to be marked, exhibits sufficient adhesive character to permit local abrasive transfer of an X-ray observable quantity of said radio-opaque substance to said surface, and wherein said radio-opaque substance consists of finely divided particles of bismuth trioxide.

2. The marker of claim 1 wherein said dispersing medium in addition contains a coloring agent.

3. The marker of claim 1 wherein said dispersing medium has a melting point above about 110° F.

4. A method for detecting, within an assembly comprising constituent textile products, the location of predetermined portions of textile product constituents comprising such assembly, which portions were identified during the manufacture or inspection of such constituents prior to the formation of such assembly, and which locations are not readily observable to the unaided eye, said method comprising the steps of (a) marking said predetermined portions prior to the formation of said assembly by applying a single radio-opaque substance consisting of bismuth trioxide thereto, said radio-opaque substance being dispersed in a dispersing medium which is a solid at room temperature but which has sufficient adhesion to allow abrasion and transfer of said radio-opaque substance to said predetermined portions whenever dispersing medium is brought into frictional contact with said predetermined portions of said constituents to be marked;

(b) forming said assembly;

(c) illuminating said assembly with X-rays; and (d) observing, with the aid of appropriate X-ray sensitive means, said locations marked with said radio-opaque substance.

5. A textile substrate having a surface comprised of textile yarns wherein a portion of an exposed perimeter of said textile yarns comprises said surface of said textile substrate wherein localized areas of said substrate surface are in contact with a waxy dispersing medium in which is dispersed a single radio-opaque substance consisting of finely divided particles of bismuth trioxide.

6. The textile of claim 5 in which said dispersing medium further contains a coloring agent.

* * * * *